United States Patent [19]

Titone et al.

[11] Patent Number: 4,667,662
[45] Date of Patent: May 26, 1987

[54] CERCLAGE DEVICE

[75] Inventors: Milo A. Titone, Newcastle, Del.;
Simone C. Titone, Birchrunville, Pa.;
John Czajka, Albany, N.Y.

[73] Assignee: Davol, Inc., Cranston, R.I.

[21] Appl. No.: 586,257

[22] Filed: Mar. 5, 1984

[51] Int. Cl.$^4$ .............................................. A61F 5/04
[52] U.S. Cl. ............................ 128/92 YD; 128/92 R
[58] Field of Search ................. 128/92 R, 92 B, 92 A, 128/335.5, 92 BC, 92 D

[56] References Cited

U.S. PATENT DOCUMENTS

| | | | |
|---|---|---|---|
| 2,987,062 | 6/1961 | Ellison | 128/92 B |
| 3,435,823 | 4/1969 | Edwards | 128/346 |
| 3,469,573 | 9/1969 | Florio | 128/92 R |
| 3,570,497 | 3/1971 | Lemole | 128/335.5 |
| 3,840,018 | 10/1974 | Heifetz | 128/92 R |
| 4,037,603 | 7/1977 | Wendorff | 128/335.5 |
| 4,119,091 | 10/1978 | Partridge | 128/92 D |
| 4,146,022 | 3/1979 | Johnson et al. | 128/92 BC |
| 4,263,904 | 4/1981 | Judet | 128/92 B |
| 4,535,764 | 8/1985 | Ebert | 128/92 E |

FOREIGN PATENT DOCUMENTS

| | | | |
|---|---|---|---|
| 3244680 | 6/1984 | Fed. Rep. of Germany | 128/92 A |
| 590290 | 6/1925 | France | 128/92 D |

Primary Examiner—Robert Peshock
Assistant Examiner—C. W. Shedd
Attorney, Agent, or Firm—Wolf, Greenfield & Sacks

[57] ABSTRACT

An orthopedic cerclage device for binding and stabilizing fractured bone segments is formed from an elongate fabric strip adapted to be tied tightly about the bone to secure the fractured bone parts together. The fabric strip has a plurality of transverse ribs raised from one face of the fabric. The strip is wrapped tightly about the bone with the ribbed surface engaging the bone. The strip is secured in place by a locking member. The primary pressure applied to the bone by the device is at the ribs so that the segments of the strip between the ribs do not adversely cut off vascular circulation in the bone. The fabric structure of the device also allows bone tissue to grow into the interstices of the device thereby incorporating it intimately into the healed bone. Also disclosed is a novel knitted fabric in which the ribs are knitted integrally into the stitch pattern of the fabric.

13 Claims, 11 Drawing Figures

CERCLAGE DEVICE

BACKGROUND OF THE INVENTION

This invention relates to orthopedic cerclage devices for use in stabilizing fractured bones. Cerclage devices, in the form of plastic or metal straps, bracing devices, wires or bands have been proposed and used to secure together and stabilize the segments of a fractured bone. The cerclage technique has advantages over more conventional techniques for stabilizing fractured bones such as skeletal traction. Skeletal traction typically requires the patient to remain in bed for a long time, often in excess of three to four months. Such prolonged period of immobilization is undesirable and can be particularly hazardous for elderly patients. Thus, there has been a need for an effective cerclage device which can avoid, or at least reduce, the requirement for skeletal traction. Although a number of cerclage devices have been proposed in recent years, and while some of them have had a limited degree of use, they have presented a number of difficulties which have detracted from their use.

For example, the earlier cerclage devices, such as the Parham steel band, were little more than wires or metal straps wrapped and secured tightly about the bone segments. In order for the Parham band to grip bone segments sufficiently tightly to stabilize them, the band would tend to be so tight about the bone as to cut off substantial portions of the vascular circulation within the bone. Cutting off circulation in the bone eventually leads to death of the affected parts of the bone and possibly the entire bone. Thus, in most instances where a Parham band or similar constricting wire has been used it was usually necessary to remove the band or wire within a number of weeks after the initial placement. That, of course, subjects the patient to a second operation with its inherent risks and complications.

In an effort to avoid the difficulties caused by the Parham steel band other cerclage devices have been proposed. One such device is described in U.S. Pat. No. 4,119,091. It is in the form of a nylon strap having small projections on its undersurface to hold the strap away from the bone. The object of the nylon device is to reduce the area of contact with the bone so as to reduce the constricting effect on the bone vascularization. That device, however, may not provide sufficient stability for the fractured bone segments. An additional difficulty presented by the prior devices which remained implanted in the patient is that as the bone heals the pressure of the device may inhibit the quality and size of the callus which forms around the region of the fracture and could affect the strength of the bone when it is healed.

Another desirable characteristic of a cerclage device is that it should be easily manipulated, placed and handled by the surgeon. The devices which have been proposed in the prior art typically have been formed from a stiff material such as metal or plastic and have had less than ideal handling characteristics.

Thus, a need has existed for an improved cerclage device for securing and stabilizing fractured bone segments. It is among the primary objects of the invention to provide such a cerclage device.

SUMMARY OF THE INVENTION

Our invention includes a cerclage device in the form of an elongate strip adapted to be wrapped tightly and secured about the fragmented bone segments. The strip is formed from a fabric. The strip is provided with a bone engaging surface and has a plurality of transversely extending fabric ribs spaced at intervals along the length of the strip. When the cerclage device is wrapped about the bone segments to be stabilized the major proportion of the constricting force is applied to the bone through the fabric ribs. The band segments between the ribs apply minimal constricting force and do not interfere with the vascularization of the bones.

The fabric is designed so that it will have interstices which enable bone tissue to grow intimately in between and through the fabric as the bone heals. This results in a stronger bone in the healed region, with reduced bulk.

The device includes a fastening clip secured to one end of the strip and which receives the other end of the strip when the strip is wrapped about the bone. The fastening clip may be clipped to lock the strip in the bone encircling configuration.

The cerclage fabric is formed of a special knitted structure, preferably a warp knit fabric. The fabric is a two-needle bar fabric and is of special construction to form the ribs while also providing an extremely strong cerclage device capable of stabilizing fractured bone segments.

In a preferred embodiment of the invention the fabric is formed on a warp knit Raschel two-bar knitting machine. The fabric may be considered as having a front panel and a back panel, formed on the front and back needle bars respectively, with the front and back panels being interconnected by a chain stitch. The front panel is a two guide bar fully threaded panel. The front panel forms the external surface of the cerclage band.

The back panel, which forms the inner ribbed surface of the cerclage device, is made on the back needle bar. The back panel is made up of two groups of yarns. The first group of yarns alternately lay in and cast stitches at predetermined course intervals. The stitches are arranged in groups along a selected course and the group of stitches at that course form a region of bulk which defines a transversely extending rib. The yarns in the second group of yarns in the back panel are laid in walewise except at that course where a rib is formed by a row of stitches. The yarns in the second group are laid in course-wise at that course. The portion of the yarns in the second group which are laid in course-wise are trapped between the underlap and overlap of the stitches formed by the first group of yarns in the back panel and form a more massive underlying support for the stitches in the first group of yarns. Thus, the course wise laid in segments of the yarns in the second group provide support and tend to raise the rib-defining stitches in the first group, thereby defining a more pronounced and reinforced walewise rib.

The front panel and back panel are connected to each other by a chain stitch associated on each needle and on each wale. The chain stitch runs front panel to back panel on every course and on every wale.

It is among the objects of the invention to provide improved orthopedic cerclage device.

Another object of the invention is to provide a cerclage device which does not cut off the bone vascularization yet which provides sufficient strength to stabilize the fractured bone segments.

A further object of the invention is to provide a cerclage device which is porous and which permits bone tissue to grow intimately into the pores of the device upon healing.

Another object of the invention is to provide a cerclage device in which the bone engaging surface of the device is defined by a fabric.

A further object of the invention is to provide a cerclage device the use of which is simplified in comparison to previous cerclage devices.

Another object of the invention is to provide a fabric for use as a cerclage device in which transverse extending longitudinally spaced ribs are formed on the fabric.

Still another object of the invention is to provide a cerclage device which is easy to handle and place by the surgeon.

DESCRIPTION OF THE DRAWINGS

The foregoing and other objects and advantages of the invention will be appreciated more fully from the following further description thereof, with reference to the accompanying drawings wherein.

DESCRIPTION OF THE PREFERRED EMBODIMENT

Figure 1:
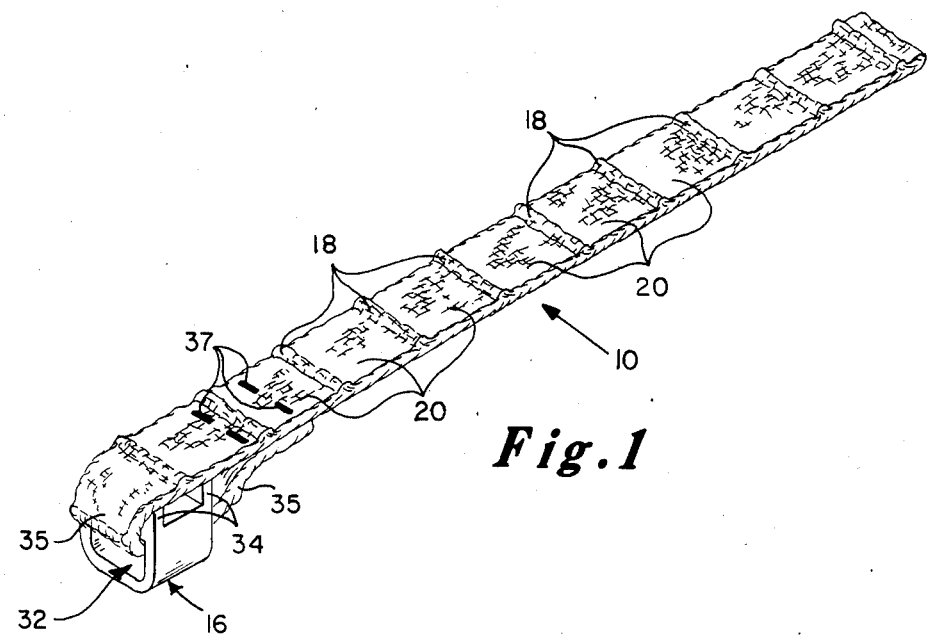
FIG. 1 is a perspective illustration of a cerclage device in accordance with the invention.
Figure 2:
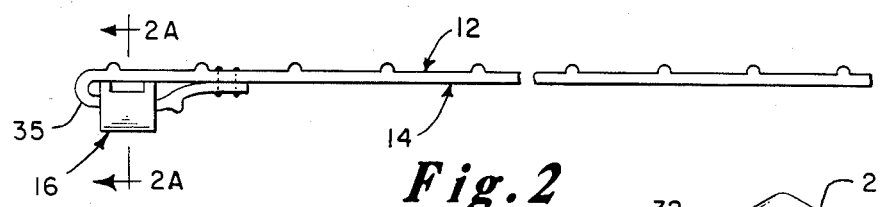
FIG. 2 is a side elevation of the device.
Figure 2A:
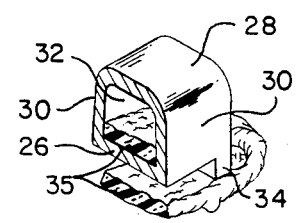
FIG. 2A is a sectional illustration of the attaching clip seen along the line 2A—2A of FIG. 2.

As shown in FIGS. 1 and 2 the device includes an elongate strip of fabric 10. The fabric may be considered as having an internal surface 12 and an external surface 14. The fabric strip preferably is provided with a fastening clip 16 which may be securely sewn to one end of the strip 10. The internal surface 12 of the strip 10 is provided with a plurality of transversely extending ribs indicated generally at 18. The ribs are spaced longitudinally along the length of the strip 10. By way of example, the ribs may be spaced about 0.75 to 1.0 cm. In the embodiment shown the ribs 18 are regularly spaced longitudinally along the strip 10 defining a series of regular intermediate segments 20. In the embodiment shown the ribs 18 extend continuously and regularly along the length of the strip. In other embodiments, however, the ribs 18 may be provided in groups in which the length of the intermediate segments 20 may vary between groups. The strip may be made in various widths, for example 0.5, 1.0 or 1.5 cm.

The height of the ribs 18 in the illustrative embodiment is substantially greater than the height of the intermediate segments 20. The ribs 18 extend substantially the full width of the strip 10.

Figure 4:
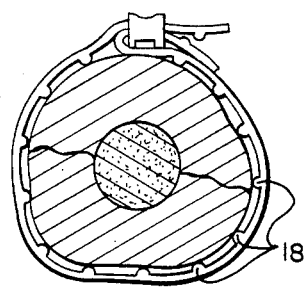
FIG. 4 is a sectional illustration as seen along the line 4—4 of FIG. 3.
Figure 3:
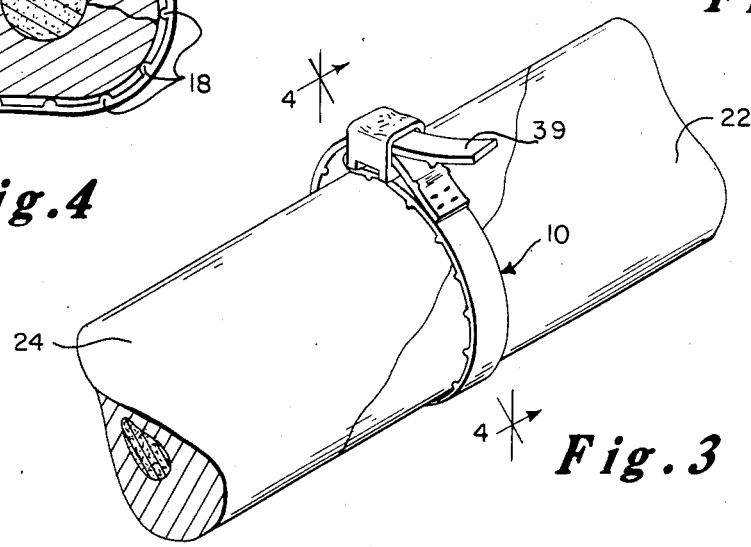
FIG. 3 is an illustration of the device secured about bone segments to stabilize the segments.

FIGS. 3 and 4 illustrate the manner in which the device is used to secure the segments of a fractured bone together to stabilize the segments while the fracture heals. After the bone segments, 22, 24 have been positioned properly with respect to each other one or more of the fabric strips 10 is wrapped about the bone, drawn tight and secured by the fastening clip 16. As illustrated more clearly in FIG. 4 the device is applied about the bone with the internal surface facing the bone so that the ribs 18 can bear against the outer surface of the bone. When the device is drawn tight and secured about the bone the ribs 18 supply the primary constricting force to the bone. Because the ribs 18 and strip 10 are formed from fabric, the ribs 18 may compress somewhat so that the internal surface 12 of the intermediate segments 20 may contact the outer surface of the bone. In the event such contact occurs it is relatively light and will not be under a sufficient pressure to have any constricting effect on the vasculature within the periosteum of the bone. The principal constricting force on the bones is applied through the ribs 18.

The fastening clip 16 may be formed from metal, such as an appropriate surgical steel which can be crimped in appropriate tools such as pliers. The clip 16 is in the form of a band having an inside wall 26, an outside wall 28 and a pair of connective sidewalls 30. The band defines an internal opening 32. A pair of transversely extending feet 34 extend from the inside wall 26 and face the external surface 14 of the strip 10. This can be seen from FIG. 4, when the device is in place the feet 34 will extend parallel to the bone, parallel to the ribs 18. The space between the feet 34 serves to reduce the area of pressure contacts which might be applied to the bone as a result of the clip 16. The clip 16 is attached to the strip 10 by a loop 35 formed at the end of the strip 10. The loop 35 is passed through the internal opening 32 in the clip 16 and the end of the loop 35 is attached to the strip 10 as by stitches 37.

As illustrated in FIGS. 3 and 4 the strip is securely wrapped about the bone by passing the free end 39 through the internal opening 32 of the clip 16, drawing the band tightly about the bone and while holding the band in tightly wrapped configuration, crimping the outside wall 28 of the clip 16 to grip securely the free end 39 of the strip 10. It may be noted that the facing portions of the strip which are received within the opening 32 of the clip 16 will engage each other ribbed surface to ribbed surface. Interlocking of the facing ribs within the clip may enhance the locking of the device in its bone encircling configuration.

As described, a preferred embodiment of the invention utilizes a fabric which is very strong, preferably in the form of a warp knit fabric and may be manufactured on a double needle bed Raschel machine. The fabric may be considered as having a front panel, knit on the front needle bed of the machine and a back panel knit on the back needle bed of the machine with the front and back panels being intimately interconnected by yarns formed in a chain stitch associated on each needle and on each wale. The chain stitch runs front panel to back panel on every course and on every wale to connect together each stitch on the front panel with a corresponding stitch on the back panel. The front panel defines the relatively smooth external surface 14 of the fabric strip 10. The back panel is formed to define the ribbed internal surface 12 of the fabric strip 10. The manufacture of a fabric in accordance with the illustrative embodiment is described below with reference to the illustrative diagrams.

Figure 5:
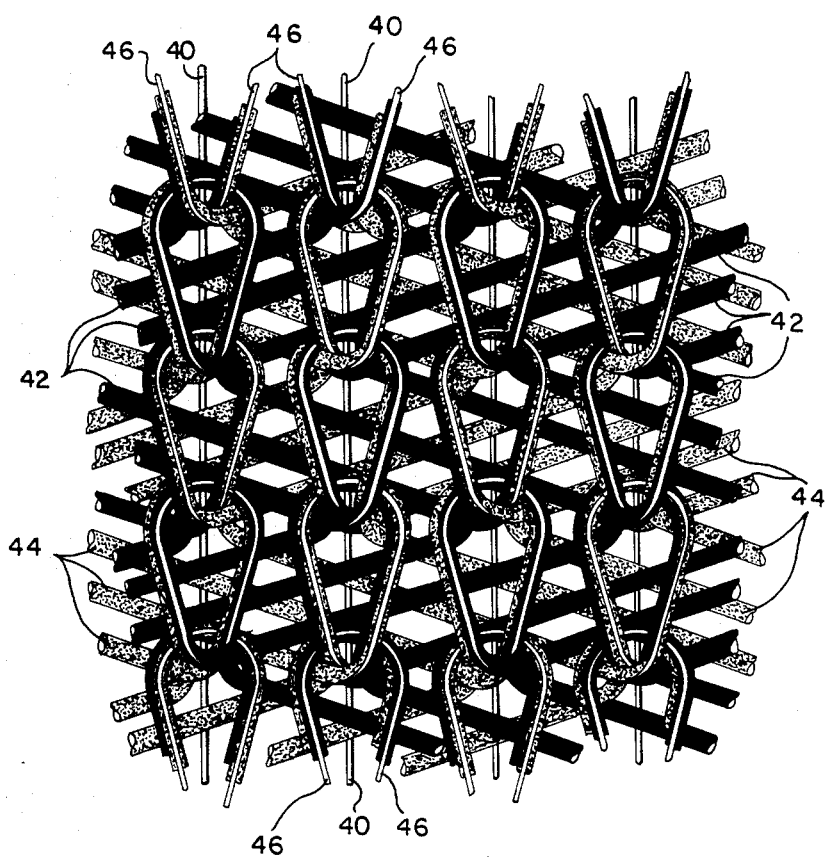
FIG. 5 is a somewhat diagrammatic illustration, greatly enlarged, the front panel of the fabric of which the cerclage device is formed and including portions of the chain stitch yarn which interconnect the front panel to the back panel of the fabric.
Figure 6:
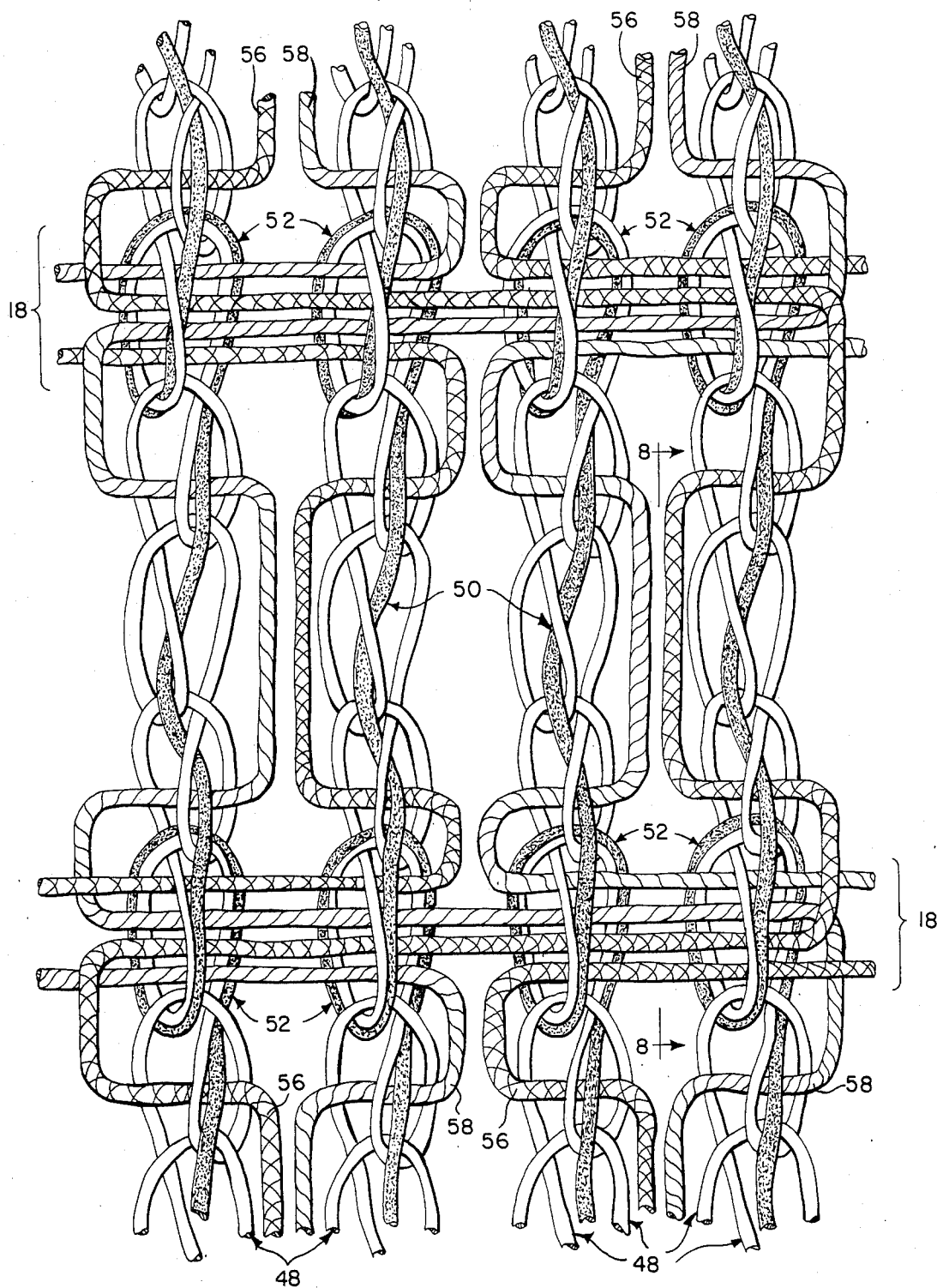
FIG. 6 is an illustration of the back panel of the fabric, greatly enlarged, with the chain stitch yarns omitted for clarity.
Figure 7:
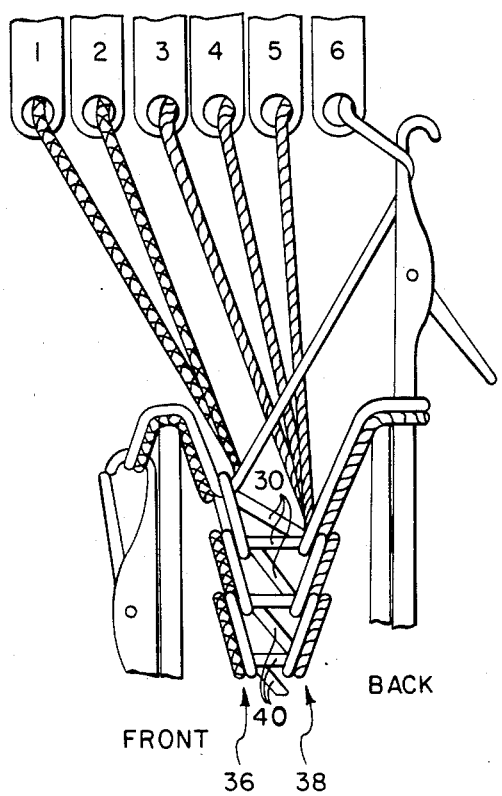
FIG. 7 is a side elevation of the needle beds and guide bars in the Raschel knitting machine illustrating the manner in which the chain stitch yarn interconnects the front and back panels of the fabric.

FIG. 5 illustrates, somewhat diagrammatically, and on an enlarged scale, the stitch configuration of the front panel, indicated generally by the reference character 36 (see also FIG. 7). FIG. 6 illustrates diagrammatically and also in greatly enlarged scale the stitch pattern in the back panel, indicated at 38 in FIG. 7. The manner in which the front panel 36 and back panel 38 are knitted together to define the composite fabric is suggested somewhat diagrammatically in FIG. 7 which illustrates the manner in which a yarn, guided by guide bar 6 and illustrated in FIG. 7 without shading is knitted in a chain stitch whose underlaps 40 run between the front and back panels 36, 38 to knit the front and back panels 36, 38 together and secure them in a unitary stable fabric.

The construction of the front and back panels 36, 38 of the fabric and their interconnection with the chain stitch yarn will be apparent to those of ordinary skill in the art from the following tables and related threading and point pattern diagrams for a Raschel machine. As is well known to those skilled in the art the Raschel knitting machines are double needle bed machines having a front needle bed and a back needle bed which rise and fall alternately in knitting action. The machine includes a number of guide bars each carrying a plurality of yarn guides, numbered 1 through 6 in FIG. 7. As is well understood by those skilled in the art the guide bars swing to and fro from the front to the back needle bars and also are moveable laterally as controlled by pattern links on a pattern chain to control all the yarn guides on that bar in unison. In the following description yarns will be referred to by the number of the guide bar which controls the yarn, thus, the unshaded yarn in FIG. 7 will be the "bar 6" yarn. As may be seen from FIG. 7 the front panel 36 is knitted from two yarns including the bar 1 yarn and the bar 2 yarn. The back panel 38 is knitted from the three yarns identified as the bar 3, the bar 4 and bar 5 yarns. The bar 6 yarn alternates between the front and back yarns, forming a chain stitch at each course and each wale to knit the front and back panels together in a unitary stable structure. It will be understood the the respective needle beds rise and fall alternately to receive yarn guided by the yarn guides carried by the guide bars, each by having as many yarn guide eyes as there are needles in a row, although various eyes may be left unthreaded.

Table I sets forth the chain readings and starting points for a preferred embodiment of the invention.

TABLE I

| GUIDE BAR NO. | PATTERN LINK | STARTING POINT BETWEEN NEEDLES |
|---|---|---|
| 1 | 6/8 | 3,4 |
| 2 | 2/0 | 1,2 |
| 3 | 2/2 | 1,2 |
| 4 | 8/8 | 4,5 |
| 5 | 0/0 | 0,1 |
| 6 | 2/0 | 1,2 |

Figures 9, 10:
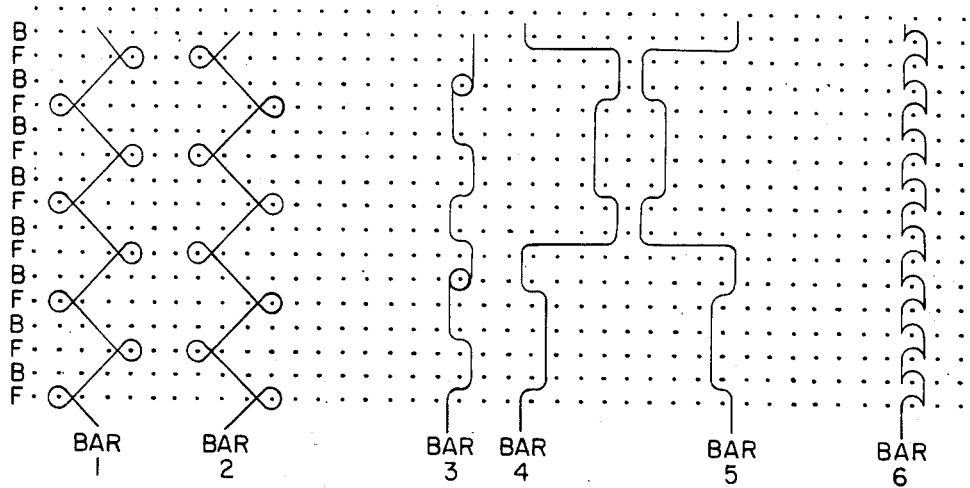
FIG. 9 is a point pattern diagram for the component yarns of the fabric.
FIG. 10 is a Raschel threading diagram for use in the manufacture of the illustrative embodiment of the invention.

FIG. 10 is a threading diagram for the Raschel machine for manufacture of the illustrative embodiment of the invention. Yarn is threaded through those guides on the respective guide bars as indicated by small circles in FIG. 10. It will be apparent to those skilled in the art that a number of strips of fabric may be made simultaneously on the same Raschel knitting machine, the number of strips which can be made being limited only by the total number of needle positions in the machine. The description herein is of a single strip and may be duplicated if it is desired to manufacture multiple strips at the same time. Table II sets forth the pattern chain readings for the chain links used to control the shogging movements of the guide bars to knit the fabric of the preferred embodiment of the invention.

TABLE II

| NEEDLEBED | GUIDE BAR NO. | | | | | |
|---|---|---|---|---|---|---|
| | 1 | 2 | 3 | 4 | 5 | 6 |
| F | 6/8 | 2/0 | 2/2 | 8/8 | 0/0 | 2/0 |
| B | 4/4 | 4/4 | 0/0 | 6/6 | 2/2 | 0/2 |
| F | 2/0 | 6/8 | 0/0 | 6/6 | 2/2 | 2/0 |
| B | 4/4 | 4/4 | 2/2 | 6/6 | 2/2 | 0/2 |
| F | 6/8 | 2/0 | 2/2 | 6/6 | 2/2 | 2/0 |
| B | 4/4 | 4/4 | 2/0 | 8/8 | 0/0 | 0/2 |
| F | 2/0 | 6/8 | 0/0 | 8/8 | 0/0 | 2/0 |
| B | 4/4 | 4/4 | 2/2 | 0/0 | 8/8 | 0/2 |
| F | 6/8 | 2/0 | 2/2 | 0/0 | 8/8 | 2/0 |
| B | 4/4 | 4/4 | 0/0 | 2/2 | 6/6 | 0/2 |
| F | 2/0 | 6/8 | 0/0 | 2/2 | 6/6 | 2/0 |
| B | 4/4 | 4/4 | 2/2 | 2/2 | 6/6 | 0/2 |
| F | 6/8 | 2/0 | 2/2 | 2/2 | 6/6 | 2/0 |
| B | 4/4 | 4/4 | 2/0 | 0/0 | 8/8 | 0/2 |
| F | 2/0 | 6/8 | 0/0 | 0/0 | 8/8 | 2/0 |
| B | 4/4 | 4/4 | 0/0 | 8/8 | 0/0 | 0/2 |

FIG. 9 is a stitch diagram for each of the six guide bars 1–6 used in manufacture of the fabric. Guide bars 1 and 2 stitch only on the front needle bed (see also FIG. 7) to form the front panel 36 of the fabric. Guide bars 3, 4 and 5 knit only on the back needle bed and in conjunction with guide bar 6 form the back panel 38. Guide bar 6 stitches alternately on both the front and back beds in a chain stitch which interconnects the front and back panels. Guide bar 6 is fully threaded and stitches continuously along each wale, alternating from the front needle bed to the back needle bed so as to connect the front and back panels at each wale along each course.

FIG. 5 depicts, somewhat diagrammatically, the configuration of stitches of a representative portion of the front panel as seen from the overlap side of the panel (from the left in FIG. 7). The panel formed on the front needle bed is a two-bar fully threaded panel. As can be seen from the stitch diagram of FIG. 9 and Table II each of the bar 1 underlaps 42 (solid in FIG. 5) and each of the bar 2 underlaps 44 (stippled in FIG. 5) crosses over four needles which adds body to the panel. The technical face of the front panel 36 as seen in FIG. 5 consists essentially of overlaps of the bar 1 and bar 2 yarns and is essentially flat and smooth. It defines the external surface 14 of the fabric strip 10. FIG. 5 also illustrates the bar 6 yarns and their overlap portions 46 as well as segments of their underlaps 40. It should be noted that in FIG. 5 the appearance of the bar 6 underlaps 40 is somewhat distorted from the appearance they would have in the composite fabric. Thus, FIG. 5 is somewhat diagrammatic and is intended primarily to illustrate the stitch pattern for the primary bar 1 and bar 2 yarns of the front panel.

Figure 8:
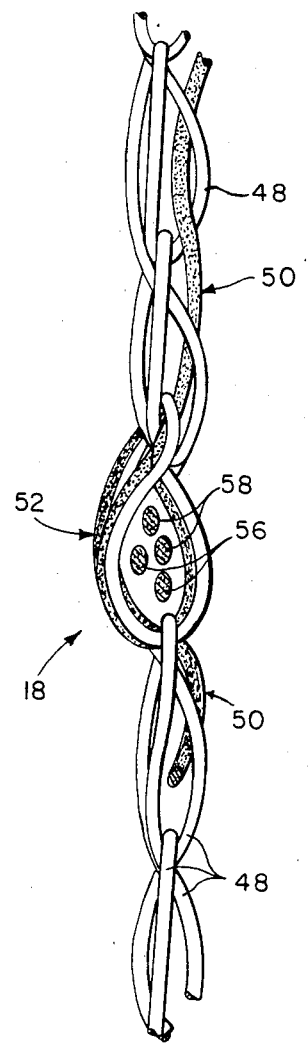
FIG. 8 is a somewhat diagrammatic side view of a portion of the back panel segment as seen along the line 8—8 of FIG. 6.

The stitch configuration for the back panel may be seen from FIGS. 6 and 8, in which FIG. 6 illustrates the back panel as seen from its underlap side (from the left in FIG. 7). In the back panel the bar 6 yarn 48 formed a continuous chain stitch along each wale. For clarity of illustration the back panel the bar 6 yarn is illustrated in a manner which omits the connection of the underlaps of the bar 6 yarn to the front panel. It will be understood that in the actual knitted fabric the underlaps of the bar 6 yarn in the back panel will have been drawn toward and knitted in a stitch in the front panel at each wale and course of the front panel as suggested in FIG. 7.

The back panel may be considered as being made up of two groups of yarns (not including the bar 6 chain stitch yarn). The first group of yarns in the back panel are the bar 3 yarns, indicated at 50 and shown in a stippled pattern which alternately lay in except with a cast stitches, indicated at 52, at predetermined intervals along the length of the fabric. The stitches 52 are arranged in groups which extend transversely along a course-wise line. Each transverse line of stitches 52 defines a line of bulk which forms the ribs 18. The second group of yarns in the back panel are those guided by bars 4 and 5. The bar 4 and 5 yarns indicated at 56 (cross hatched) and 58 (unshaded), respectively, are laid in yarns. The bar 4 and 5 yarns 56, 58 are laid in walewise except where they reach the region of the rib 18, defined by the row of stitches 52 of the bar 3 yarn. At the region of the transverse row of stitches 52 the bar 4 and 5 yarns are laid in course-wise and are trapped between the underlap and overlap of the stitches 52 formed by the first group of yarns (the bar 3 yarns). Thus the bar 4 and bar 5 yarns 56, 58 form a more massive underlying support for the stitches 52 in the first group of yarns (bar 3) and help to raise and define the wale-wise extending ribs 18. FIG. 8 illustrates in side view the manner in which the bar 4 and bar 5 yarns 56, 58 are laid in course-wise and are trapped between the underlap and overlap of the stitches 52 so as to provide a raised supported region of bulk to define a transversely extending rib 18.

Although, as may been seen from the stitch diagram, tables and notations the ribs are spaced at each four courses in the illustrative embodiment, other spacings may be developed as may be desired.

It is preferred that the yarns used in the back panel 38 are substantially heavier than the yarns in the front panel 36 and the bar 6 chain stitch yarn. Use of comparatively heavier yarns to form the transverse row of stitches 52 and the underlying course-wise filler results in a firmly supported and well defined rib capable of transmitting the necessary pressures to the bone to stabilize it.

Although the preferred embodiment contemplates use of coursewise fillers formed from yarns knitted into the fabric, in some instances it may be desired to provide a supplemental or substitute filler extending transversely of the fabric. In all cases, however, it is important that the bone-engaging internal surface 12 of the device be in the form of a fabric face capable of defining a multiplicity of interstices into which bone tissue may grow.

From the foregoing it will be appreciated that the cerclage device provides numerous advantages over the prior devices. It should be understood, however, that the foregoing description of the invention is intended merely to be illustrative of the invention and that other modifications and embodiments may be apparent to those skilled in the art without departing from its spirit.

Having thus described the invention what we desire to claim and secure by letters patent is:

1. A cerclage device for binding together and stabilizing fractured segments of a bone comprising:
   an elongate flexible member having an inner surface and an outer surface, said member being adapted to be wrapped about the bone with its inner surface facing the surface of the bone;
   means enabling the member to be securely fastened about the bone so as to stabilize the fractured segments of the bone;
   the bone engaging inner surface of the member being formed from a fabric composed of a plurality of yarns arranged to define a multiplicity of interstices between the yarns;
   a plurality of ribs defined on the inner surface of the strip, said ribs extending transversely and being spaced longitudinally along the strip, said ribs being adapted to bear against the outer surface of the bone when the device is tied about the bone, said ribs serving to provide the primary pressure points at which the constricting force of the device is applied to the bone.

2. A device as defined in claim 1 wherein the strip is formed from a knitted fabric.

3. A device as defined in claim 2 further comprising:
   said knitted fabric being a warp knit double needle bed Raschel fabric having a front panel and a back panel, said front and back panels being intimately interconnected by yarns formed in a chain stitch associated on each needle and on each wale, said chain stitch running front panel to back panel on every course and on every wale to connect together each stitch on the front panel with a corresponding stitch on the back panel;
   said front panel defining a relatively smooth external surface of the fabric strip;
   said back panel defining the ribbed internal surface of the fabric strip.

4. A device as defined in claim 7 wherein the fabric further comprises:
   said front panel being knitted from a first yarn and a second yarn knitted in a two bar fully threaded pattern in which the underlaps of each yarn cross over a plurality of wales;
   said back panel including third, fourth and fifth yarns, said third yarns extending along each wale, said third yarns being laid in except for cast stitches formed at predetermined coursewise intervals along the length of the fabric, said stitches being arranged in groups extending transversely along a coursewise line;
   said fourth and fifth yarns being laid in in a walewise direction except in the region of said rows of stitches formed by said third yarns, said fourth and fifth yarns being laid in coursewise at the region of said rows of stitches of said third yarns, said fourth and fifth yarns being trapped between the underlap and overlap of the stitches formed by said third yarns;
   said coursewise rows of stitches each defining a transversely extending rib, said coursewise laid in portions of said fourth and fifth yarns providing additional support for and reinforcing said ribs; and
   a sixth yarn forming a chain stitch at each course and on each wale of each of said front and back panels, the underlaps of each of said chain stitches running front panel to back panel to knit said front and back panels together in an integral fabric.

5. A device as defined in claim 4 wherein the underlaps of said first and second yarns in said front panel cross over and include four wales.

6. A device as defined in claim 5 wherein each of said first, second and sixth yarns is lighter than any of said third, fourth and fifth yarns.

7. A device as defined in claim 4 wherein said third yarn is heavier than said first, second and sixth yarns.

8. A device as defined in claim 4 wherein said fourth and fifth yarns are heavier than said first, second and sixth yarns.

9. A device as defined in claim 4 wherein said third, fourth and fifth yarns are heavier than said first, second and sixth yarns.

10. A device as defined in claim 1 wherein the strip is formed in its entirety from yarns and wherein the ribs are formed by arranging the yarns in a pattern in which a plurality of yarns are grouped together in a more compact configuration at spaced intervals along the length of the strip.

11. A device as defined in claim 3 wherein said fabric further comprises:
said more compacted configuration of yarns being defined by a plurality of coursewise extending rows of stitches formed in the fabric, said rows of stitches being formed only at spaced intervals in a walewise direction along the fabric.

12. A device as defined in claim 4 wherein said ribs further comprise:
a plurality of yarns laid in coursewise at each row of rib-defining stitches, said crosswise laid in yarns being trapped between the overlaps and underlaps of the stitches in each of said rib-defining groups, said walewise laid in yarns adding further support and height for the rib-defining stitches.

13. A device as defined in claim 5 further comprising:
the outer surface of the elongate flexible member being knitted from yarns in a pattern in which its technical face is exposed exteriorly thereby defining a relatively smooth outer surface.

* * * * *